(12) United States Patent
Schulat et al.

(10) Patent No.: US 7,566,419 B2
(45) Date of Patent: Jul. 28, 2009

(54) MAGAZINE FOR HOLDING TEST ELEMENTS

(75) Inventors: Jochen Schulat, Mannheim (DE); Josef Mueller, Kirchberg (CH); Hansjoerg Braendle, Niederuzwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 3 days.

(21) Appl. No.: 11/439,835

(22) Filed: May 24, 2006

(65) Prior Publication Data

US 2007/0007183 A1    Jan. 11, 2007

(30) Foreign Application Priority Data

May 24, 2005    (EP)    .................................. 05011188

(51) Int. Cl.
*G01N 33/00*    (2006.01)
(52) U.S. Cl. .................................................... 422/68.1
(58) Field of Classification Search ................. 422/68.1
See application file for complete search history.

(56) References Cited

U.S. PATENT DOCUMENTS 3,918,910 A * 11/1975 Soya et al. ..................... 422/66

| 6,534,017 | B1 * | 3/2003 | Bottwein et al. ............ 422/104 |
| 2002/0057993 | A1 | 5/2002 | Maisey et al. |
| 2002/0076349 | A1 | 6/2002 | Aitken et al. |
| 2003/0002387 | A1 | 1/2003 | Bottwein et al. |
| 2003/0191415 | A1 | 10/2003 | Moerman et al. |

FOREIGN PATENT DOCUMENTS

| DE | WO 98/47007 | * | 4/1998 |
| EP | 1 321 769 | | 6/2003 |
| EP | 1321769 | | 6/2003 |
| EP | 1 507 143 | | 2/2005 |
| EP | 1507143 | | 2/2005 |
| EP | 1 529 488 | | 5/2005 |
| EP | 1529488 | | 5/2005 |
| WO | WO 02/18940 | | 3/2002 |
| WO | WO 02/055008 | | 7/2002 |

* cited by examiner

*Primary Examiner*—Walter D Griffin
*Assistant Examiner*—Bobby Ramdhanie
(74) *Attorney, Agent, or Firm*—Baker & Daniels LLP

(57) ABSTRACT

A portable analysis appliance includes a housing and a magazine for holding test elements. A delivery device is provided for delivering the test elements from a first position in the interior of the magazine to a second position lying at least partially outside the magazine and inside the housing. The delivery of the test elements including a first movement out of the interior of the magazine and a second movement by means of a guide into a presentation position.

34 Claims, 10 Drawing Sheets

Fig. 4.1
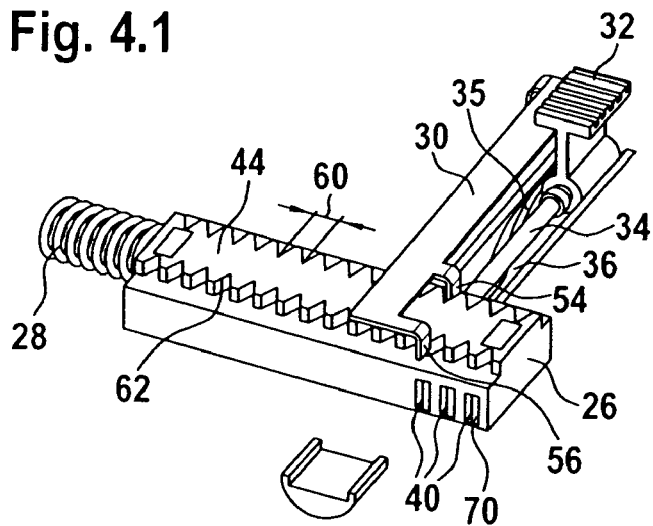
Fig. 4.2
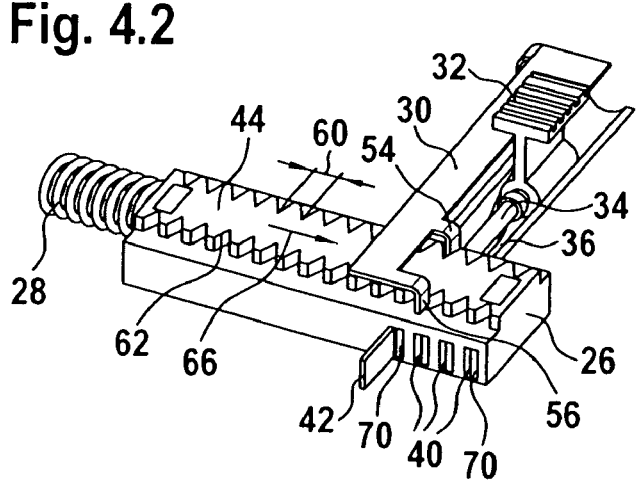
Fig. 4.3
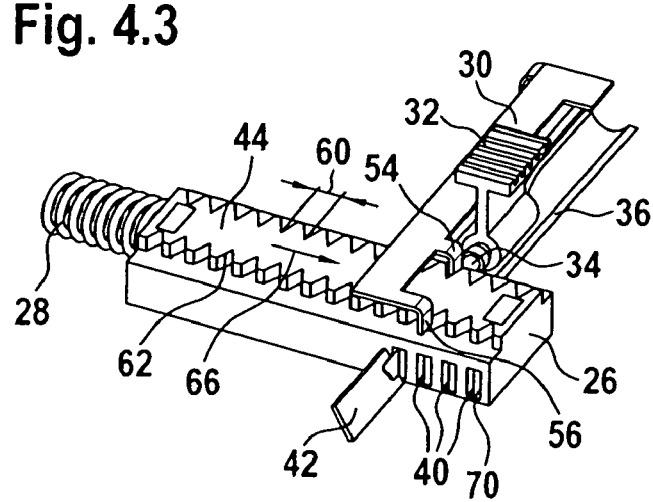

Fig. 4.4
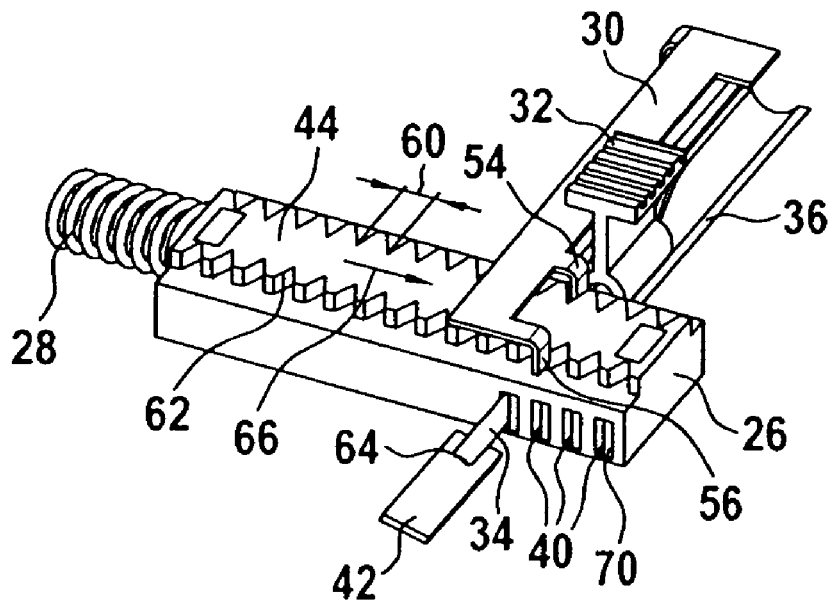
Fig. 4.5
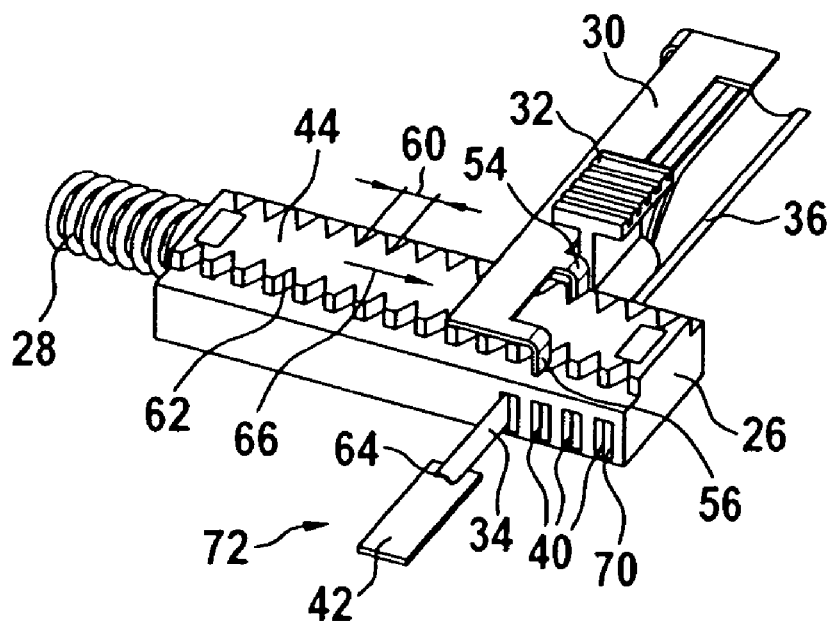

Fig. 5.1
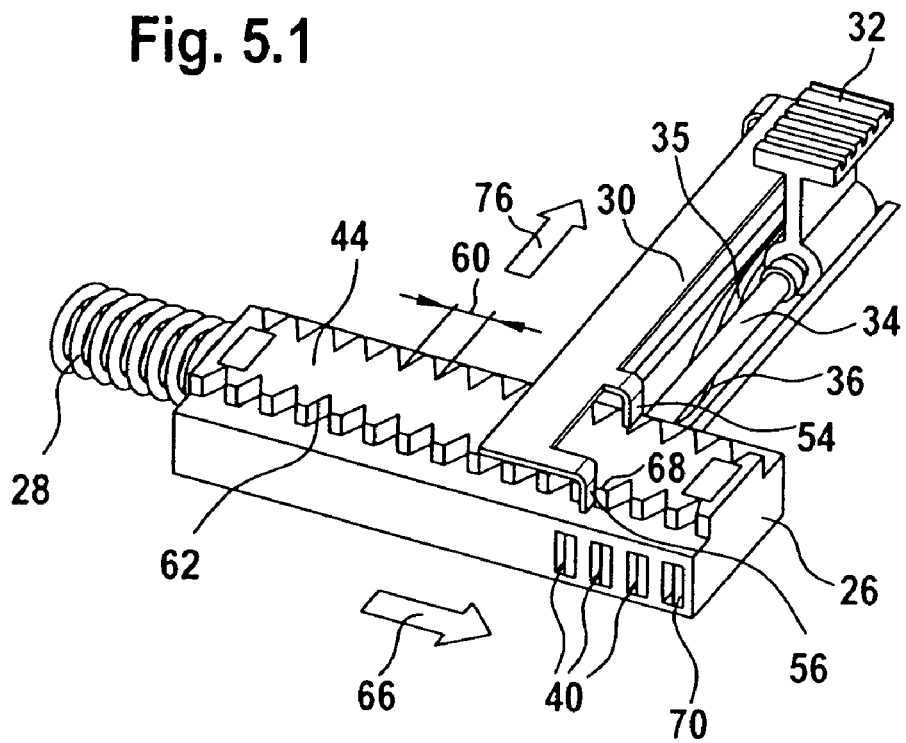
Fig. 5.2
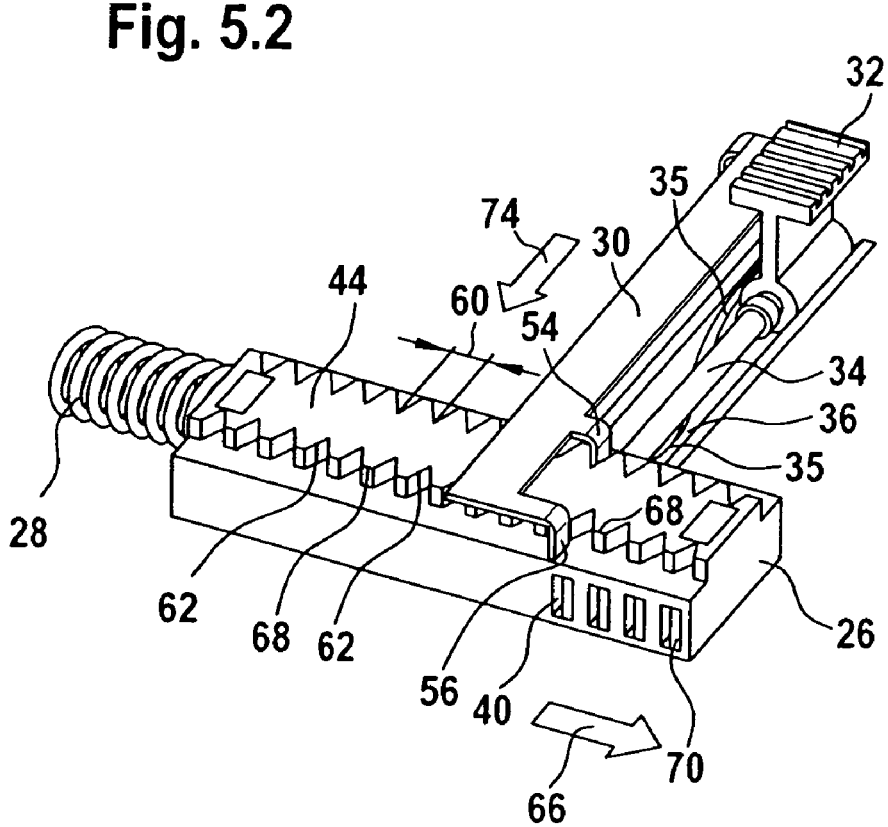

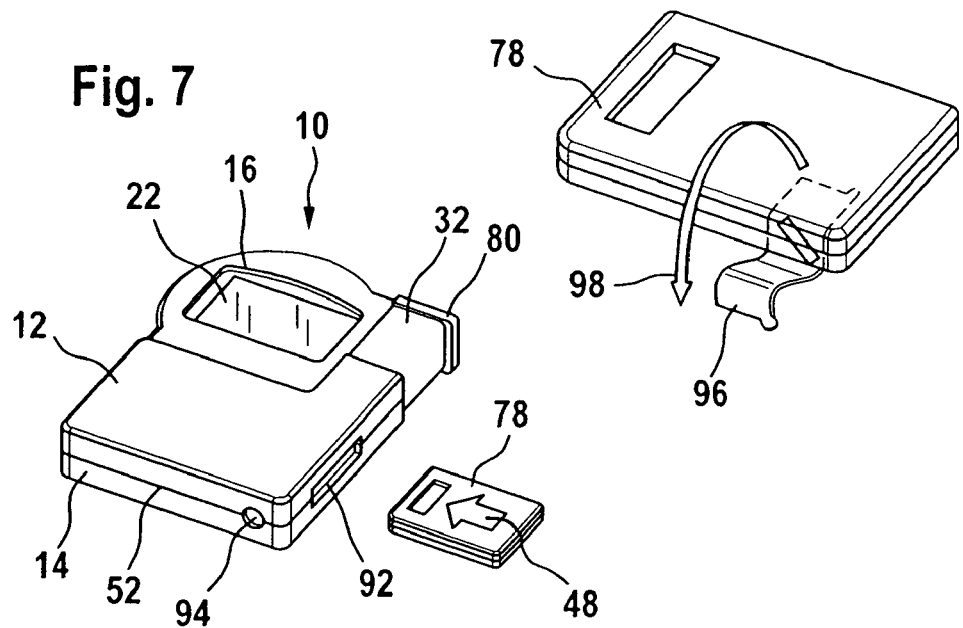
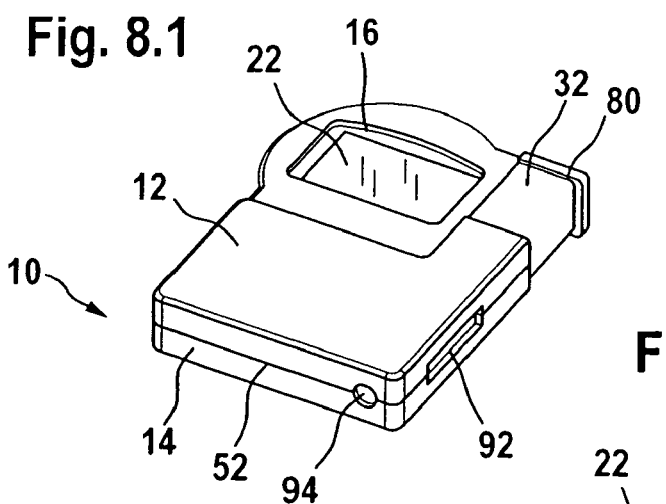
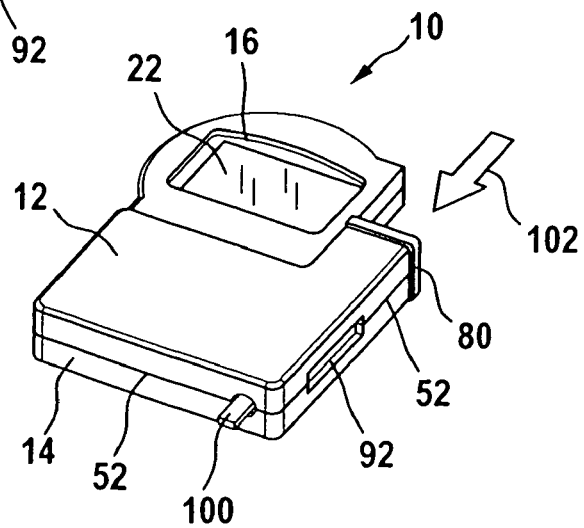

Fig. 9.1
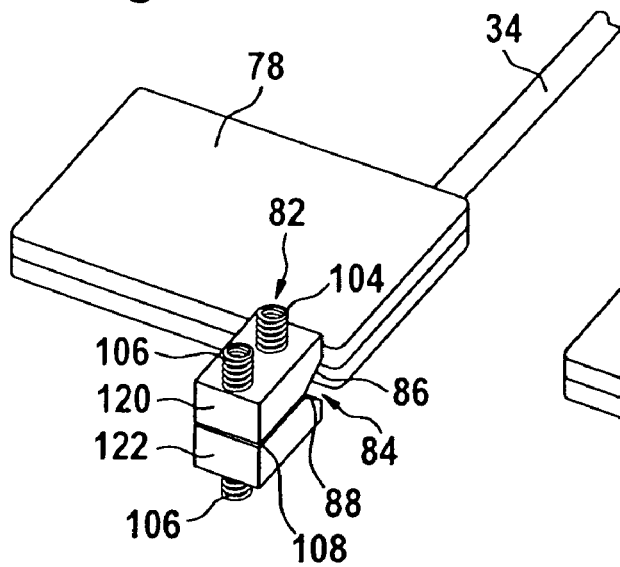
Fig. 9.2
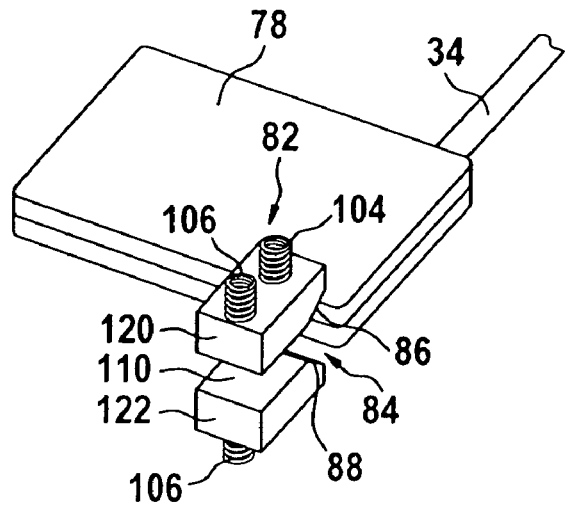
Fig. 9.3
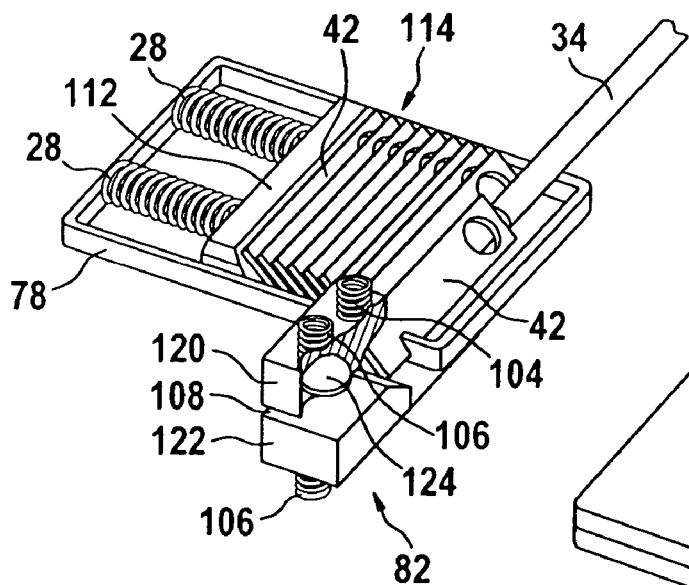
Fig. 9.4
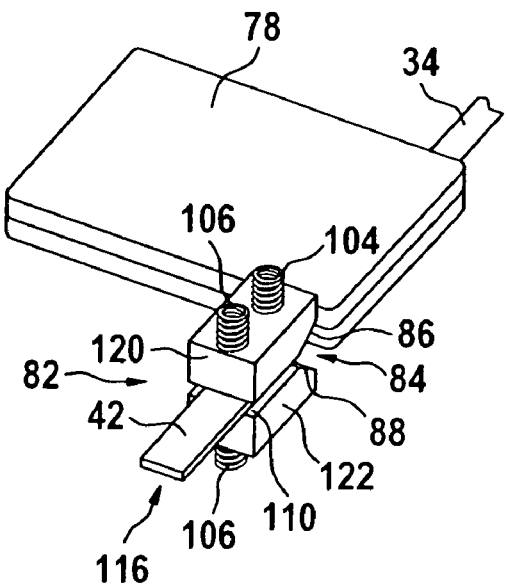

Fig. 9.5
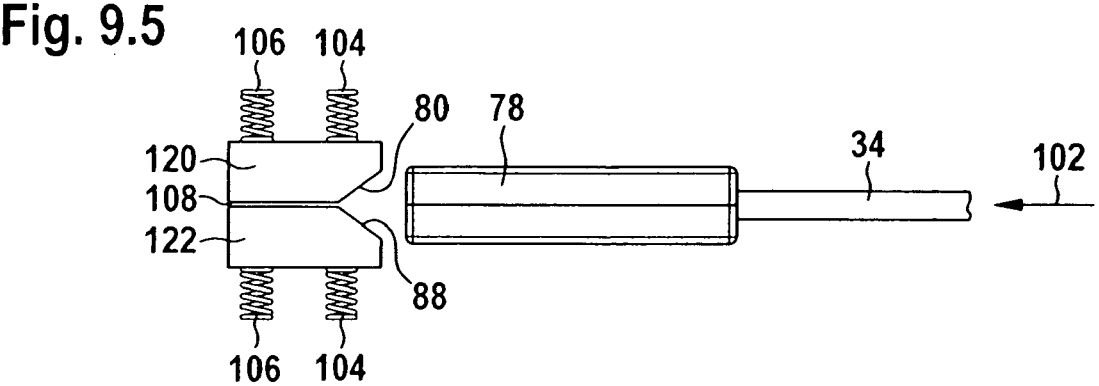
Fig. 9.6
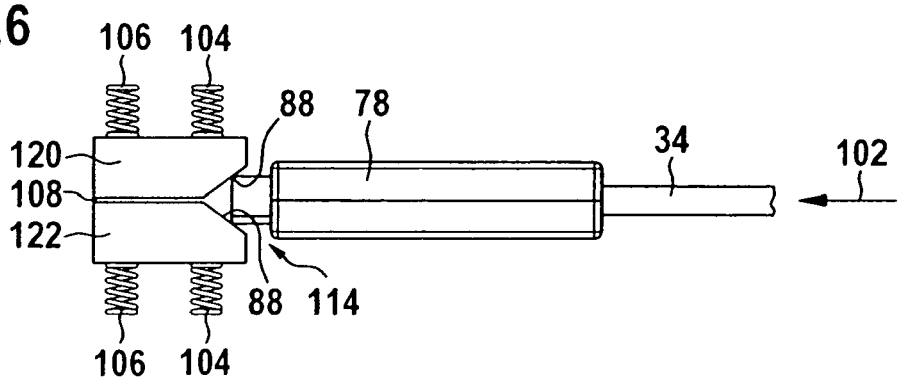
Fig. 9.7
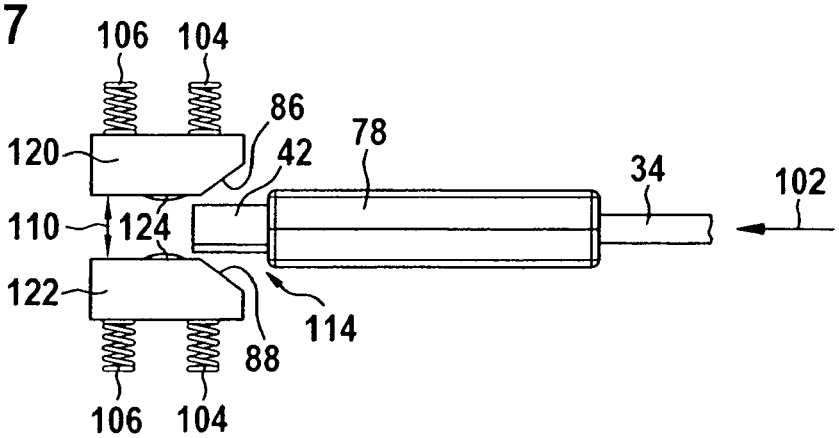
Fig. 9.8
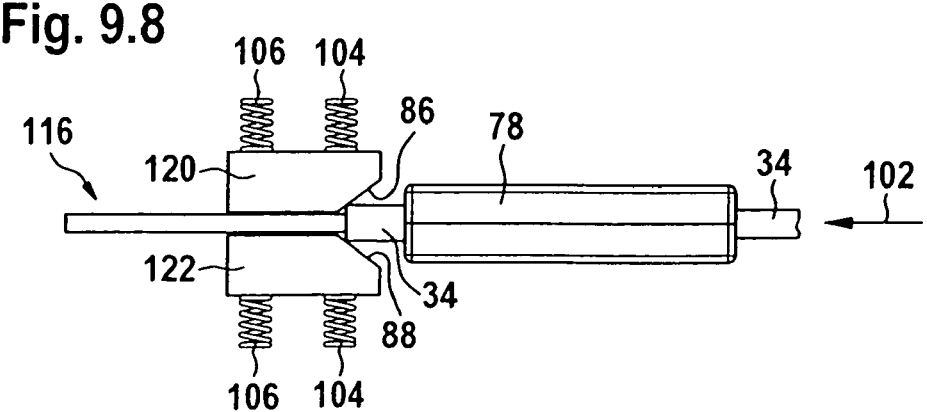

Fig. 10.1
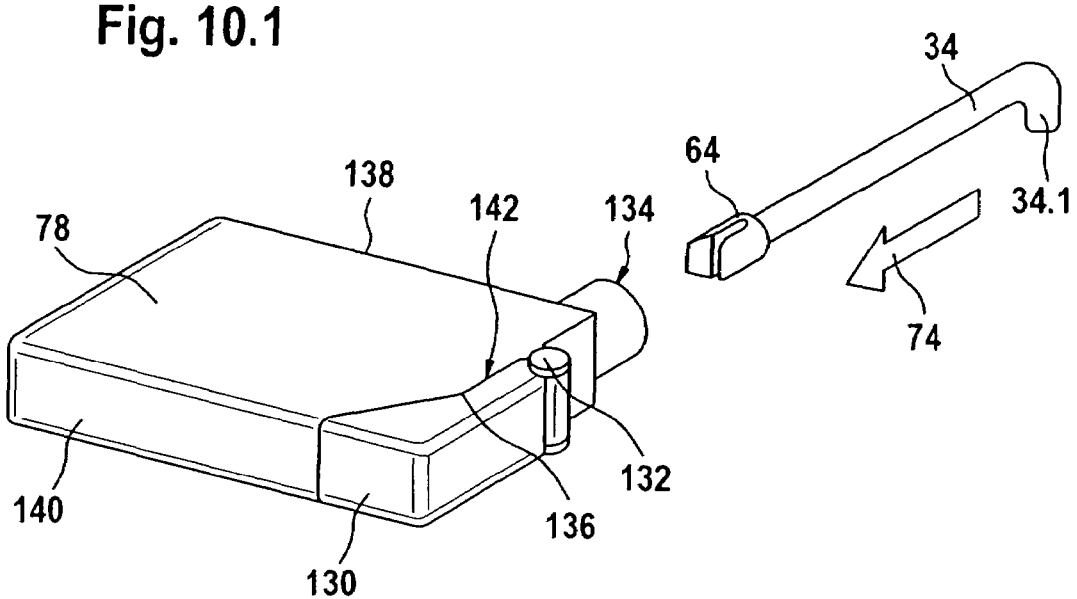
Fig. 10.2
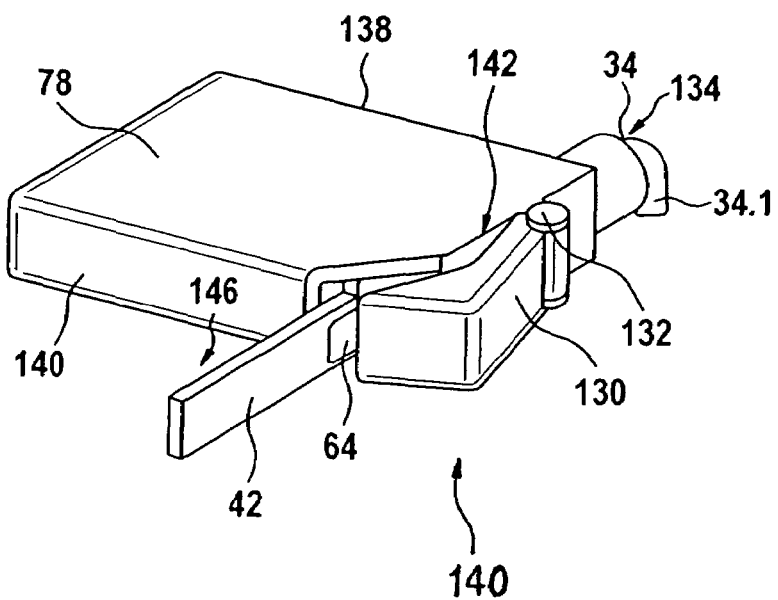

MAGAZINE FOR HOLDING TEST ELEMENTS

FIELD OF THE INVENTION

The invention relates to a magazine for holding medical consumable articles, the magazine being able to be used particularly in a portable analysis system for analysis of a human body fluid.

BACKGROUND OF THE INVENTION

EP 1 321 769 A1 discloses an appliance with a dispenser device. The dispenser device comprises a housing with a chamber. A number of test strips are held in a first position in which they are substantially airtight and sealed off against moisture. Means are provided for opening the chamber and for moving one of the plurality of test strips in a translation direction from the first position inside the chamber to at least a second position lying partially outside the chamber. The chamber is opened and the one test strip moved out in a single mechanical movement. Moreover, an analysis device is provided for analyzing a biological fluid.

WO 02/18940 A2 discloses a test device. The test device is used to examine a fluid for the concentration of an analyte that it contains. A housing has an opening and contains a stack of sensors. A transport element is mounted rotatably in the opening of the housing and has a rotation axle that engages in the opening. The stack is pressed against the transport element by means of a spring. Sealing means are also provided which permit a moisture-tight seal between the transport element and the sensors when the transport element moves into a specific rotation position. An outer surface of the transport element has a recess which is configured in such a way that an individual sensor can be taken from the stack. A rotary movement of the transport element, with a sensor held in the recess, transports the sensor to a position in which the sensor can be connected to a measurement appliance and takes up a drop of the fluid that is to be tested.

In previous measurement appliances, for example for determining the glucose content of blood, individual medical consumables designed as test strips can be pushed by hand into the measurement appliance by the person using said measurement appliance. The individual test strips and the measurement appliance are transported separately from one another. The number of test strips that the person using the measurement appliance carries on his person is assigned a code key containing batch-specific chemical information needed for correct determination of the glucose content of a human body fluid, for example blood, and this information is transmitted to the measurement appliance. This code key has to be fed into the measurement appliance prior to the measurement. To make the complicated handling of test strips, code key and measurement appliance easier for the end users, measurement appliances exist which comprise a test strip magazine that can be inserted into the appliance. Such appliances are known from the prior art documents EP 1 321 769 A1 and WO 02/18940 A2 mentioned in the introduction. In accordance with these solutions, batch-specific information can be carried with the magazine and can be read out automatically by the measurement appliance.

As regards the solutions known from the prior art, a disadvantage is that said solutions involve relatively large dimensions, which means that the measurement appliances, into which a magazine with several test strips held in it is inserted, have a relatively large volume. This, however, is highly undesirable for the end user, because measurement appliances are intended to be carried about relatively inconspicuously on one's person and are intended to be designed for instance in the manner of a pocket calculator or mobile phone, so as to make it easier for the end user to handle such measurement appliances and in particular to carry them about. A further disadvantage is that the measurement appliances have a format that is not very user-friendly and the presentation position of the test element is not the optimal position, which fact makes the handling of such appliances more difficult.

SUMMARY OF THE INVENTION

The present invention provides a stack magazine which affords the possibility of the test elements contained in it being arranged in a high packing density. This makes it possible not only to give the portable analysis appliance small dimensions, but also to accommodate a greater number of test elements in the exchangeable magazine. A code key is integrated on the magazine and is automatically read out when the magazine containing the test elements is inserted into the portable analysis system. By means of the code key integrated in the magazine, batch-specific information relating to the chemical substances contained on the test elements is transferred that is necessary for correct determination of the analyte in question, for example the glucose content of blood, and is transmitted to the portable analysis appliance. By integration of this code key on the magazine, the patient is spared the awkward handling of several components, i.e. test element, code key and appliance, because the code key and the magazine holding the number of test elements represent one structural part.

The magazine proposed according to the invention, for example configured in a stack form, affords the possibility both of automatic and also manual provision of the test elements. If in particular a magazine form is chosen that can be manually operated, it is then also possible to dispense with drive mechanisms and with the energy sources that are needed for these, with the result that the portable analysis appliance can additionally be made much smaller and more robust. Systems hitherto known from the prior art, for example of drum-shaped design, require a separate and in most cases electrically configured drive mechanism to permit their rotation movement.

To avoid air moisture getting into the interior of the portable analysis appliance and into the interior of the stack-shaped magazine, sealing elements made of an elastic material, for example rubber, are used. These are opened during transport of the test element from the for example stack-type magazine inside the portable analysis appliance or analysis system. When the rubber lips are opened by the test element, the entry of air moisture into the interior of the stack-type magazine is caused by the test element itself emerging from said magazine. The moisture that could penetrate into the interior of the magazine upon pressure on the sealing elements, for example sealing lips, made of elastic material, is absorbed by a desiccant, for example silica gel, present inside the for example stack-type magazine.

According to a first embodiment of the stack-type magazine proposed according to the invention, the test elements can be held in slit-shaped hollow spaces. By means of a manually actuated ram, the individual test elements are pushed out from the hollow spaces which can each be closed by elastic sealing elements along the side by which the ram moves into the stack-type magazine and along the outlet side of the stack-type magazine. The long sides of the stack-type magazine can be sealed off by a thin lacquer layer or a film seal that prevents entry of air moisture into the hollow spaces in which test elements are held. The sealing lacquer or the film seal is pierced either by the ram at the admission side or by the test element itself.

The magazine, which can be designed in a stack form for example, comprises a toothed structure in which a transport pawl engages. By means of the transport pawl, the stack-type magazine acted upon by a pretensioning element is moved in the interior of the portable analysis appliance such that, upon each actuation by the patient, a new, unused and sealed test element is ejected by means of the manually actuated ram. According to this embodiment, the individual test elements are held inside the magazine in a vertical orientation, i.e. upright. The ram that pushes the test elements out from the hollow spaces of the magazine is guided in a guide that imparts a turning movement to the ram. After the test element has been pushed out from the hollow space inside the magazine, a turning movement is imparted to the ram and to the test element received on the front face of the ram. The turning movement of the ram with the test element held on it occurs only after the test element has completely exited the respective hollow space inside the magazine. Thus, the test element is transferred from its storage position, in which it can assume a vertical orientation, to a horizontal position, i.e. the test element is turned through 90° after it has been pushed out from the magazine. In this 90° position in relation to the orientation of the test element in the magazine, the test element emerges from the portable analysis appliance at an output opening. As a result of the turning of the test element after it has been pushed out from the magazine, it is possible for a greater number of test elements to be accommodated in each magazine, i.e. the packing density of the test elements is considerably increased compared to a horizontal arrangement of the test elements in the magazine. Furthermore, after its for example 90° turn, the test element lies in the same plane as the display screen of the portable analysis appliance or portable analysis system. This presentation position in which the test element has been turned through 90° permits the patient or user of a test appliance to see at a glance the blood application site on the test element and also the display screen of the test appliance. It is further ensured in this way that the test appliance is simple to operate both for a right-handed person and also for a left-handed person. In the presentation position, the test strip lies parallel to the display screen, i.e. in a horizontal plane, because the blood application area in the presentation position lies on the top face of the test element. By contrast, if the test element were to be in a vertical orientation in the presentation position, then the patient or the person using the test appliance would be forced to turn the test appliance through 90° in order to find the blood application site and then turn it back through 90° to be able to read off the result on the display screen of the test appliance. Depending on the direction of turning and on the dexterity of the user, the handling of the test appliance would be made more difficult in this case.

The magazine provided according to the first embodiment with a toothed engagement structure for a transport pawl is transported by means of the transport pawl inside the portable analysis appliance. The transport pawl is actuated via a grip element held on the ram for pushing out the test element, and the magazine is in this way advanced in such a way that a new, unused and outwardly airtight sealed test element lies opposite the ram that can be actuated via the grip element for the next ejection process.

According to a further illustrative embodiment of the solution proposed according to the invention, a magazine containing test elements can be pushed into the portable analysis appliance or analysis system. Inside this magazine, the test elements are stacked in an inclined position, i.e. at an angle of approximately 45° in relation to the base surface of this magazine. Instead of the 45° angle, an angle of 30°, 60°, or other suitable angle could also be chosen. Inside the magazine, the test elements arranged in an inclined position are pretensioned by a spring-actuated surface which, when the inclined test element is removed from the magazine, pushes the next test element forwards so that the latter is ready for the next removal procedure upon manual actuation of a ram by a stamp or the like. After insertion of the magazine in which the test elements are in an inclined position, the next test element can be removed from the magazine. Before inserting the magazine into the portable analysis appliance or portable analysis system, a flap on the magazine is opened to uncover an output opening for the test element. The magazine opened at the output opening is now pushed laterally into the portable analysis appliance or portable analysis system. A guide is located opposite the outlet opening of the test element oriented in an inclined position inside the magazine. The guide comprises, for example, two mutually opposite, resiliently mounted abutment faces. Each of these resiliently mounted abutment faces comprises a run-in bevel. Because of the resilient mounting of the two abutment faces in relation to one another, a variable gap width is possible between a narrow gap between the abutment faces and a wide gap. As soon as the leading end of the test element reaching the guide, oriented at a 45° inclination, reaches the run-in bevels of the two resiliently mounted contact faces, the further advance of the ram during the ejection movement of the test element from the magazine means that the gap between the two mutually opposite abutment faces widens. When the test element has been pushed completely out of the magazine by the ram, the test element, under the effect of the springs provided on the mutually movable abutment faces, is transferred from its 45° position to a horizontal position, (i.e., is turned through approximately 45°).

Analogously to the first illustrative embodiment, the test element pushed out from the magazine now lies in a plane, i.e. a horizontally extending plane, parallel to the display screen arranged on the portable analysis appliance or analysis system. By virtue of this presentation position in which the test element lies parallel to the display screen present on the portable analysis appliance or analysis system, both the blood application area of the test element and also the display screen of the portable analysis appliance or analysis system can be seen at a glance, without the portable analysis appliance or analysis system having to be turned by the patient or the user. In this way, the portable analysis appliance or portable analysis system can be used both by a right-handed person and by a left-handed person with a high level of operating comfort. It is now no longer necessary to turn the appliance round in order to see the blood application area of the test element and no longer necessary to turn it back again to read off the measurement result on the display screen of the portable analysis appliance or analysis system.

With the solution proposed according to the invention, it is possible to optimize the packing density of test elements inside a magazine and to ensure that the particular test element to be used emerges from the portable analysis appliance or portable analysis system in an orientation that affords optimal handling for the user.

This is ensured by the common feature of the illustrative embodiments outlined above, namely by the turning of the test element inside the portable analysis appliance or portable analysis system. The turning of the test element, whether through 90° or 45°, inside the analysis appliance is obtained by manual actuation thereof, which actuation means that the ram functioning as an ejector imparts both a reciprocating movement and also a turning movement subsequent to the reciprocating movement. This is achieved through just one actuating manoeuvre by the patient or user and brings the test element into an optimal position for use.

BRIEF DESCRIPTION OF THE DRAWINGS

The invention is described in more detail below with reference to the drawings, in which:

FIG. 7 is a perspective view of the portable analysis appliance or analysis system in the assembled state, FIG. 7.1 is a perspective view of a detail view of the magazine that can be pushed into the portable analysis appliance according to FIG. 7, with lateral detaching flap, FIG. 8.1 is a perspective view of the portable analysis appliance according to FIG. 7 with the ejection device not actuated, FIG. 8.2 is a perspective view of the test element pushed out from the portable analysis appliance according to FIG. 7 by actuation of a plunger, FIG. 9.1 is a perspective view of the magazine containing the test elements in an inclined position, together with a guide, FIG. 9.2 is a perspective view of the guide with a test element pushed out from the magazine, FIG. 9.3 is a perspective view of the interior of the magazine according to the view in FIG. 7.1, FIG. 9.4 is a perspective view of a test element that has been turned to a horizontal position, held by the guide, and FIGS. 9.5 to 9.8 are side elevational views of several stages in the turning of the test element about an axis inside the guide of the portable analysis appliance according to FIG. 6, and FIGS. 10.1 and 10.2 are perspective views of a flap-shaped sealing element for long-term sealing of a magazine arranged in a stationary state in the housing.

DETAILED DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
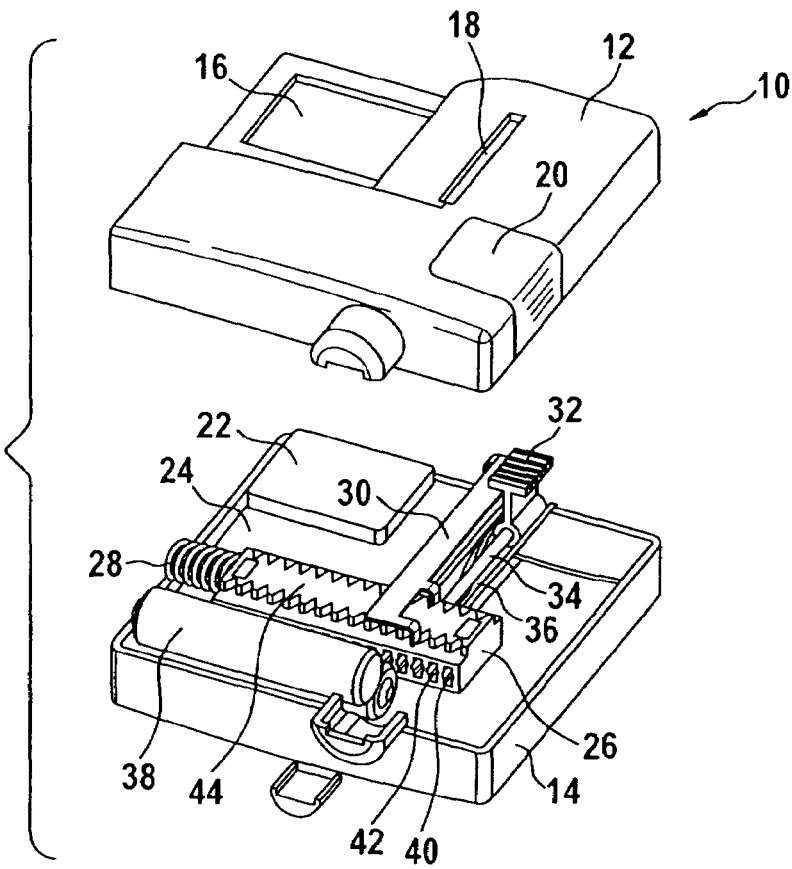
FIG. 1 is an exploded perspective view of a portable analysis appliance in a first embodiment, with the upper shell and lower shell shown separated from one another, together with the internal components.

FIG. 1 is an exploded view showing a first illustrative embodiment of a portable analysis appliance with a magazine containing test elements.

In the text that follows, measurement appliances or analysis appliances are understood as portable appliances that a user can carry around on his person at all times. Such transportable measurement appliances or analysis appliances contain a long-term energy accumulator which powers the evaluation electronics contained in the portable measurement appliance or in the portable analysis appliance. Test elements inside the portable measurement or analysis appliance can be evaluated by electrochemical means or also by optical means. In the case of optical evaluation electronics, a test element, for example a test strip, is scanned by a number of beams, whereas, in an electrochemical evaluation of a test element for an analyte contained in a body fluid, the test element comprises certain test chemicals.

In the context of electrochemical evaluation of test elements, these preferably flat or strip-shaped test elements have a base film and a carrier film with a reagent layer. Conductor tracks for connection of electrodes run inside the carrier film. The aforementioned reagent layer that contains the test chemicals can be held above the conductor tracks. Measurement chambers or measurement capillary spaces can be formed between the reagent layer and a spacer film which covers the reagent layer in separate areas. The electrochemical measurement chambers or measurement capillary spaces can be covered by a hydrophilic layer, which in turn is covered by a cover film. For removing air from the electrochemical measurement cells, a vent can be run through both the cover film and the hydrophilic layer arranged under the latter.

The electrochemical measurement cell delimited on one side by the spacer film and on the other side by the reagent layer and the hydrophobic layer receives electrodes which, for example, are arranged lying opposite one another. The electrodes include a counter-electrode CE and a further electrode WE. These can, for example, engage with one another in a comb formation. In addition, electrochemical measurement cells can be assigned fill-state electrodes FSE, in which case an individual electrochemical measurement cell can in each case at all times be assigned a pair of fill-state electrodes FSE.

The test elements can by contrast also be designed as electrochemical capillary sensors. Such a capillary sensor carrier comprises a stiffer base film with a conductive structure, electrode surfaces, conductor tracks and contacts. A reagent film with the reagents needed for the desired measurement reaction is applied over the stiffer base film in the area of the electrodes. A punched spacer film can be applied, for example bonded, onto this. This spacer film in turn forms, on one side of the capillary sensor carrier, a capillary open to this side and also an electrochemical measurement cell over the electrode surface and, at the same time, on the other side at the ends of the conductor track, contact faces permitting electrical contact. Finally, a cover film can then be bonded onto the applied, for example bonded, reagent film, which cover film closes off the capillaries at the top and at the inner end of the capillaries forms a vent hole.

The evaluation of the individual test elements, whether by optical means or by electrochemical means, preferably takes place inside the measurement appliance or analysis appliance. The evaluation can also be carried out when the test elements containing the human body fluid to be evaluated have been drawn partially into the interior of the measurement or analysis appliance.

A portable analysis appliance 10 comprises an upper shell 12 and a lower shell 14. Formed in the upper shell 12 there is an opening 16 through which a display screen 22 can be read when the portable analysis appliance 10 is in the assembled state. The upper shell 12 of the portable analysis appliance 10 according to FIG. 1 also comprises a slit-shaped opening 18. A removable closure flap 20 is also integrated into the upper shell 12 of the portable analysis appliance 10.

The display screen 22, which is held on a circuit board 24 only symbolically indicated here, is situated in the lower shell 14 of the portable analysis appliance 10. A magazine 26 in the form of a stack magazine, which is acted upon by a pretensioning spring 28, is also located in the lower shell 14. The magazine 26 is moved by means of a transport pawl 30 inside the portable analysis appliance 10. The magazine 26 is equipped with a number of test elements 42. The magazine 26 contains a desiccant, for example silica gel, and is sealed off in an airtight manner from the outside by means of applied films or a sealing layer, so that entry of air moisture into the interior of the magazine 26 is ruled out. The sealing elements sealing off the interior of the magazine 26, either in the form of thin films applied along the sides or in the form of a sealing lacquer or the like, are of such a nature that they can be pierced by an advancing device, for example a ram 34.

The transport pawl 30 extends parallel to a ram 34 that can be actuated by means of a grip element 32. The ram 34 in turn is enclosed by a guide 36 which imparts a turning movement to the ram 34 after it has passed through the magazine 26. The lower shell 14 of the portable analysis appliance 10 also accommodates energy accumulators 38 which supply electrical energy to the portable analysis appliance 10.

The magazine 26 advantageously designed as a stack magazine comprises a plurality of receiving spaces 40 for test elements 42, these receiving spaces 40 being arranged substantially in a vertical orientation. On the top face of the magazine 26 there is an engagement structure 44 into which catch teeth formed on the transport pawl 30 engage. This is described in more detail below.

In the text that follows, test element 42 is understood as an element containing reagents with which a human body fluid can be tested for an analyte. The human body fluid can be blood for example, either whole blood or thinned blood, or other body fluids. The test element 42 can additionally have a puncture function, embodied for example by a lancet integrated in the test element 42 and by a dispenser for lancets. The test element 42 can also be an integrated test element in which an evaluation circuit is integrated completely or partially on the test element. The evaluation circuit can, for example, comprise organic electronics using OFETs. Integrated test elements can additionally contain an optics system, and also excitation light sources, for example OLEDs as light sources. Moreover, an energy source in the form of an integrated SuperCAP can be integrated into integrated test elements. Integrated test elements are distinguished by a high number of integrated functions.

While the test elements 42 can also have a puncture function as an integrated function in the form of an integrated lancet, the puncture aids can also be stored separately. The puncture aids designed as lancets can, for example, be arranged in a drum-shaped magazine and be held independently of the test elements in the measurement appliance. As regards the puncture aids in the form of lancets, a new puncture aid can be made available for each application, i.e. for each single use. However, applications of a portable analysis appliance are also conceivable in which one and the same puncture aid can be used several times.

Figure 2:
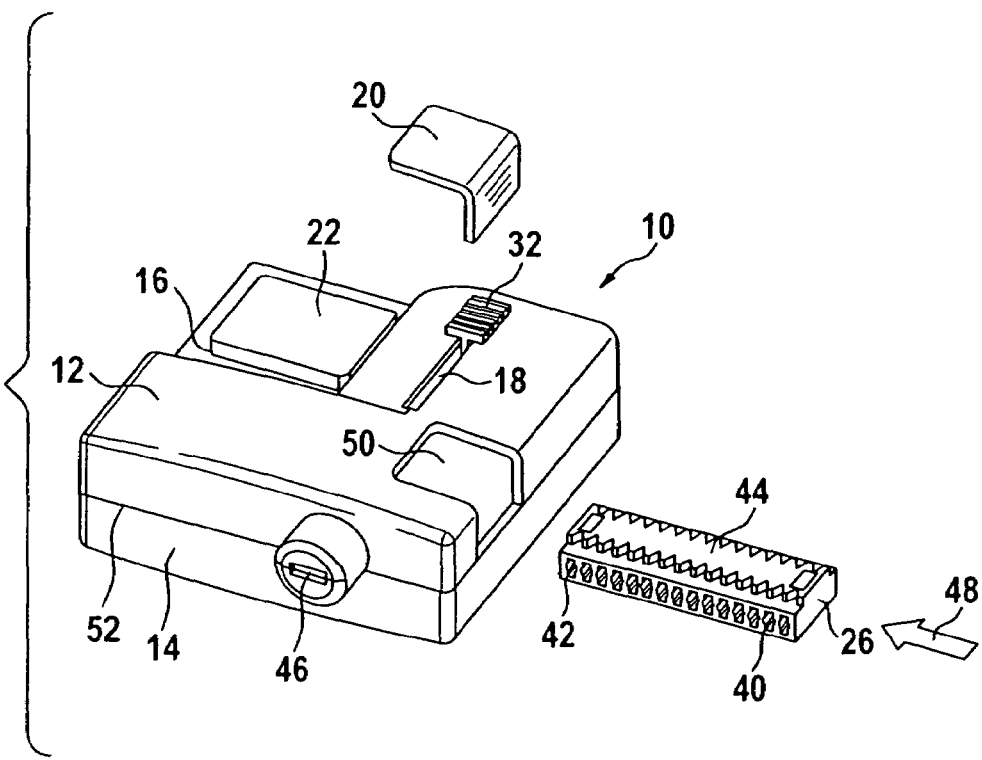
FIG. 2 is a perspective view of the portable analysis appliance according to FIG. 1 in the assembled state, with the magazine ready to be pushed in the insertion direction.

FIG. 2 shows the portable analysis appliance in the assembled state, according to the illustrative embodiment shown in FIG. 1. From the view in FIG. 2, it will be seen that the display screen 22 extends through the opening 16 of the upper shell 12. The grip element 32 for actuating the ram 34 is displaceable inside the slit-shaped opening 18. An insertion opening 50 is exposed by removal of the closure flap 20, so that the magazine 26 containing the test elements 42 can be pushed in insertion direction 48 into the portable analysis appliance 10. An output opening 46 for the test elements 42 is delimited by semi-cylindrical areas that can each be injection-moulded onto the upper shell 12 and lower shell 14. On its long sides, seen in relation to the insertion direction 48, the still unused magazine 26 has seals in order to avoid entry of air moisture into the receiving spaces 40, which are oriented substantially vertically and in which the test elements 42 are contained.

Figure 3:
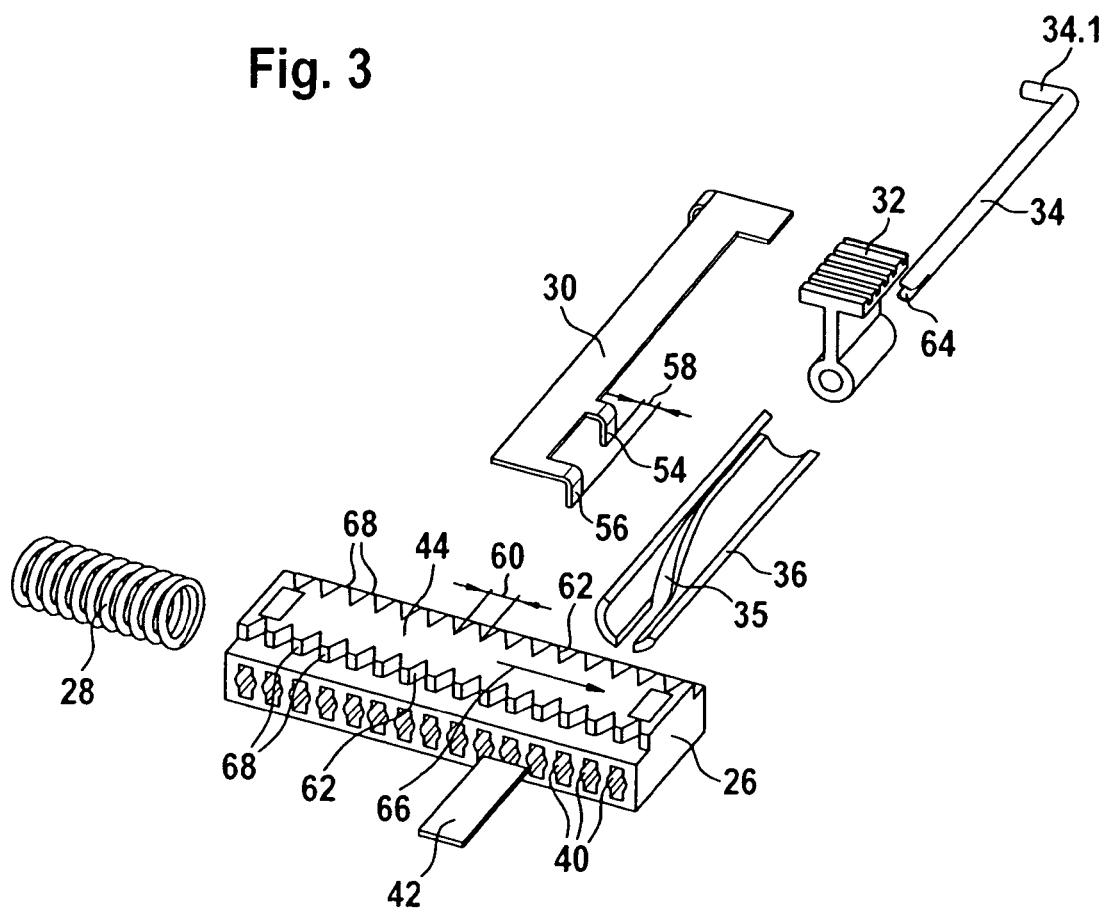
FIG. 3 is an exploded perspective view of the components of an ejection device for the test elements and a transport pawl for advancing the magazine, FIGS. 4.1, 4.2, 4.3, 4.4 and 4.5 are perspective views of the ejection of the test element and, following the ejection, the turning of the test element about an axis from a vertical position to a horizontal position, FIGS. 5.1 and 5.2 are perspective views of the advance of the magazine in the forward stroke and return stroke of the transport pawl.

FIG. 3 shows the components of an ejector mimic and of a transporter mimic for the magazine.

The ram 34 has a bent end 34.1 and, on its face directed towards the magazine 26, a receiving slit 64. The slide-shaped grip element 32 is mounted on the ram 34 by means of a sleeve-shaped attachment piece, such that the ram 34 is movable upon manual actuation of the slide-shaped grip element 32. The ram 34 with the slide-shaped grip element 32 mounted on it can be moved in a guide 36 formed in the lower shell 14 of the portable analysis appliance 10. On the inner side of the guide 36, there is a curve section 35 which imparts a turning movement to the ram 34 after it has travelled through a hollow space 40 of the magazine 26 and has pushed out the test elements 42 from the latter. The transport pawl 30 serving to advance the magazine 26, preferably a stack magazine, in the advance direction 66 has a first catch tooth 54 and a second catch tooth 56. The first catch tooth 54 and the second catch tooth 56 are arranged with an offset 58 relative to one another on the transport pawl 30. The catch teeth 54, 56 engage in the engagement structure 44 formed on the top face of the magazine 26, which can be designed as a stack magazine. In the view according to FIG. 3, the engagement structure 44 is designed as a multiplicity of teeth which are arranged in a division 60 relative to one another. The teeth of the engagement structure 44 are defined by run-in bevels 62 and abutment faces 68 and are formed on both long sides of the engagement structure 44. As will also be seen from the view in FIG. 3, the individual receiving spaces 40 of the magazine 26 have a substantially vertical orientation and have, approximately at the centre, a widened area that permits passage of the ram 34 as it is driven into the receiving space 40 of the magazine 26. As soon as the ram 34 has travelled through the magazine 26 perpendicular to the latter's advance direction 66, the respective test element 42 pushed out from the receiving spaces 40 is turned to the horizontal position shown in FIG. 3, this being effected by the curve section 35 on the inner side of the guide 36.

As can be seen from the view in FIG. 3, a guide for the test elements 42 comprises the ram 34 with a bent end 34.1 and the guide 36 in which the ram 34 is guided. After the test element 42 has been pushed out of the magazine 26, the curve section 35 arranged inside the guide 36 turns the ram 34 to a presentation position. A guide is understood hereinafter as a device which moves the test elements 42 from their upright position, in which they are stored inside the magazine 26, into a position in which they have been turned relative to the upright position.

FIG. 3 also shows the main components of the delivery device of the test element 42, with which the test elements 42 are delivered from the magazine 26. This includes the ram 34 and the grip element 32 coupled to it. The expression "delivery device" is understood as meaning devices with which a test element 42 can be pushed out of the magazine 26, which delivery device can be designed to be actuated manually or can also operate automatically.

The ejector mimic for the test elements and the transporter mimic for the magazine are shown in more detail in FIG. 4.1.

In the view according to FIG. 4.1, the magazine 26 containing the test elements 42 is transported by the transport pawl 30 into a defined position inside the portable analysis appliance 10 and is locked in said position. For this purpose, the first catch tooth 54 engages on the side of the engagement structure 44 facing it, said engagement structure being designed in a division 60. In this way, a displacement of the magazine 26, preferably designed as a stack magazine, inside the portable analysis appliance 10 is not possible. When manually actuated, the slide-shaped grip element 32 guided in the slit-shaped opening 18 pushes the ram 34 into that receiving space 40 of the magazine 26 lying opposite the front face of the ram 34 and pushes the test element 42 contained therein (compare view according to FIG. 2) out of the receiving space 40. During the advance movement of the ram 34, the curve section 35 formed on the inner side of the guide 36 has no effect. During the advance movement of the ram 34, upon manual actuation of the slide-shaped grip element 32, the ram 34 does not turn.

In the position of the magazine 26 shown in FIG. 4.1, it is locked counter to the action of the pretensioning spring 28 because the first catch tooth 54 is engaged in the engagement structure 44. Reference number 70 designates a sealing element made of elastic material, for example a lip-shaped sealing element, which, when the magazine 26 is in the unused state, is formed both on the long side facing towards the ram 34 and also on that side of the magazine 26 directed towards the output opening 46 (compare FIG. 2). Instead of the lip-shaped sealing elements 70 shown in FIG. 4.1, the long sides of the magazine 26 can also be coated with a sealing film or with a sealing lacquer, which avoids penetration of air moisture into the receiving spaces 40 of the magazine 26 and accordingly ensures that the test element 42 contained therein is not contaminated by moisture. In addition, a desiccant (not shown in the figure), for example silica gel, is received in the interior of the stack-type magazine 26.

It will be seen from the view according to FIG. 4.2 that the slide-shaped grip element 32 and, accordingly, the ram 34 connected to it have pushed the test element 42 along an axis partially out of its receiving space 40 in the magazine 26. Because of the orientation of the receiving spaces 40 in the magazine 26, the test element 42 in this state is situated in a substantially vertical position, i.e. the test element 42 is upright when pushed out of the receiving space 40.

Upright position is hereinafter understood as meaning that the test elements 42 are situated in a substantially vertical position, standing on one of their long sides. The test elements 42 are preferably of strip-shaped design, so that a very high packing density can be achieved by this position of the test elements 42 inside the magazine 26 characterized by an upright orientation. The expression upright position is hereinafter understood both as a perpendicular position of the test elements 42 relative to a supporting surface of the magazine 26 and also as an orientation of the test elements 42 inclined at an angle on a reference surface of the magazine 26.

During the movement by which the test element 42 is pushed out of the receiving space 40 of the magazine 26, the lip-shaped sealing elements 70 arranged on both sides of the outlet opening of the receiving space 40 bear on the surfaces of the test element 42 and thus suppress penetration of air moisture into the interior of the magazine 26. The air moisture that inevitably enters the interior of the magazine 26 as the test element 42 is pushed out is absorbed by the aforementioned supply of desiccant, for example silica gel, held in the interior of the magazine 26. Also in the view according to FIG. 4.2, the magazine 26 is locked in its position by the first catch tooth 54 engaging in the engagement structure 44 and is acted upon by the compressed pretensioning spring 28 in the respective position of the magazine 26 in the interior of the portable analysis appliance 10. While the first catch tooth 54 is located in an engagement structure 44 space delimited by two run-in bevels 62, the second catch tooth 56 bears on an abutment surface 68 (FIGS. 5.1 and 5.2) on the opposite side of the engagement structure 44. A movement of the magazine 26 in the advance direction 66 is thus suppressed.

It will be seen from FIG. 4.3 that, after it has been pushed out along an axis from its respective receiving space 40, the test element 42 held by the slit-shaped receiving opening 64 is turned about its longitudinal axis, starting from its vertical position. It adopts its presentation position 72 in which it has been turned through 90° relative to its storage position in the magazine 26 and therefore (compare view according to FIG. 2) lies parallel to the display screen 22 provided on the upper shell 12 of the portable analysis appliance 10. The ram 34 comprises a bent end 34.1 (compare view according to FIG. 3) which, upon actuation of the grip element 32 and driving of the ram 34 in the guide 36, runs onto the curve section 35 formed on the inside wall of the guide. In this way, the ram 34 is imparted a turning movement which begins only when the test element 42 has been pushed completely out of the hollow space 40 of the magazine 26. To guarantee the advance movement of the ram 34 inside the guide 36 with the curve section 35 formed therein, the grip element 32 is secured on the ram 34 in the longitudinal direction by abutment on the outer circumferential face of the ram 34 or by an annular shoulder or the like, and the sleeve portion formed at the lower end of the grip element 32 and enclosing the ram 34 allows a turning movement between the grip element 32 and the ram 34. This relative movement in the circumferential direction of the ram 34 effects the turning of the ram 34, and of the test element 42 held thereon, as soon as the bent end 34.1 of the ram 34 runs onto the curve section 35, which is the case only after the test element 42 has been pushed completely out of the hollow space 40 of the magazine 26. In this way, the test element 42 reaches the presentation position 72 shown in FIG. 4.5.

Presentation position 72 is understood as the position of the test element 42 in which the test element 42 emerges from the measurement or analysis appliance 10 and is presented for use to the user. The presentation position 72 is characterized in that the test element 42 in its presentation position 72 is substantially parallel to, or at a slight incline or tilt in relation to, the display screen 22 contained on the top face of the measurement or analysis appliance 10. The test element 42 moves from its storage position to the presentation position 72 by turning either about its longitudinal axis or the axis of movement of the test element 42 out of the magazine 26. It should be understood that this longitudinal axis may be the same as the axis of movement. In the presentation position 72, the user can apply a body fluid to the test element 42 and is also able to read the display screen 22 of the measurement or analysis appliance 10, without having to turn the measurement or analysis appliance 10 around. The presentation position 42 thus greatly facilitates the handling of a measurement or analysis appliance 10, since the latter no longer has to be turned round, because the presentation position 72 lies in an optimal position for the user.

In the position of the magazine 26 shown in FIG. 4.3 too, said magazine 26 is locked in its position inside the lower shell 14 of the portable analysis appliance 10 by means of the first catch tooth 54. On the one hand, this avoids jamming of the ram 34 that has been pushed into the corresponding receiving space 40, and, on the other hand, the extent of the receiving space 40 in the magazine 26 is utilized as a guide surface for the ram 34. In the position of the test element 42 shown in FIG. 4.3, the lip-shaped sealing element 70 on the output face of the magazine 26 has no effect. The test element 42 gripped by the ram 34 and pushed out of the receiving space 40 no longer has to be encapsulated in this state, because the user has actuated the slide-shaped grip element 32 for pushing the test element 42 out at the output opening 46 of the portable analysis appliance 10 and, therefore, the use of the test element 42 is directly imminent.

FIG. 4.4 shows the continued turning movement of the test element 42 starting from the position shown in FIG. 4.3.

Compared to the initial phase of the turning movement according to FIG. 4.3, the test element 42 according to the view in FIG. 4.4 has been turned almost to its presentation position 72 (compare FIG. 4.5). The turning movement takes place after the slide-shaped grip element 32 has been pushed against the long side of the magazine 26. In the view according to FIG. 4.4 too, the magazine 26 is fixed in its position inside the portable analysis appliance 10 counter to the action of the pretensioning element 28, because the first catch tooth 54 is engaged in the toothed engagement structure and prevents a lateral movement of the magazine 26 in the advance direction 66.

The division 60 on both long sides of the engagement structure 44 is advantageously configured such that the division 60, in which the gaps between the individual teeth are formed on both long sides of the engagement structure 44, corresponds to the spacing of two adjacent receiving spaces 40 of the magazine 26. In the view according to FIG. 4.4 too, the second catch tooth 56 of the transport pawl 30 bears on an abutment face 68 of a tooth on that side of the engagement structure 44 lying opposite from the slit-shaped grip element 32.

It will be seen from the view in FIG. 4.5 that, after a complete advance movement of the ram 34 and after completion of the turning movement from its storage position inside the magazine 26 to the position shown in FIG. 4.5, the test element 42 has experienced a 90° turn and is thus located in its presentation position 72.

The storage position of the test elements 42 inside the magazine 26 is characterized in that the individual test elements 42 are located in airtight hollow spaces 40 prior to use. In their storage position, the test elements 42 are held substantially in an upright orientation inside the magazine 26. In the storage position of the test elements 42 inside the magazine 26, they can be stored perpendicular to the base of the magazine 26 and can also be held at an angle inclined relative to the base of the magazine 26.

The 90° turn of the test element 42 is identified by reference number 72 in the view according to FIG. 4.5 and corresponds to the presentation position. The slide-shaped grip element 32 actuating the ram 34 bears against a long side of the magazine 26 in the position shown in FIG. 4.5. The full length of the guide 36 partially enclosing the ram 34 has been travelled, such that, in this position, the end of the medical consumable article accessible to the user in the form of a test strip 42 has been driven out of the output opening 46 on the portable analysis appliance 10 according to the view in FIG. 2.

The advance of the magazine 26 inside the portable analysis appliance 10 can be seen from the views according to FIGS. 5.1 and 5.2.

It will be seen from the view according to FIG. 5.1 that, because of the offset 58 of the first catch tooth 54 and second catch tooth 56 on the transport pawl 30 as shown in FIG. 3, the second catch tooth 56 engages in a gap between the teeth of the engagement structure 44, while the first catch tooth 54 in the view according to FIG. 5.1 bears on an abutment surface identified by reference number 68 on the opposite long side of the engagement structure 44. The movement of the transport pawl 30 takes place via a coupling with the manually actuated grip element 32. The coupling between the transport pawl 30 and the grip element 32 can, for example, be via a spring coupling or a latch mimic, such that the transport pawl 30 is coupled to the grip element 32 only during the initial phase of the latter's advance movement and ensures an onward indexing of the magazine 26 in the advance direction of said magazine 26, as is designated by reference number 66. The onward indexing of the magazine 26, in whose hollow spaces 40 the test elements 42 are held, can take place both during the movement of the transport pawl 30 as designated by reference number 76 in FIG. 5.1 and also during the reciprocating movement of the transport pawl 30 as indicated by reference number 74 in FIG. 5.2. After the test element 42 has been pushed out of the hollow space 40 of the magazine 26, the catch teeth 54, 56 each engaging in the indents of the engagement structure 44 ensure that the next hollow space 40, as seen in the advance direction 66 of the magazine 26, is positioned opposite the ram 34 that can be moved by means of the grip element 32, so that in the next use cycle, i.e. at the next actuation of the grip element 32, it can be pushed out of its hollow space 40 in the magazine 26.

On the long side of the magazine 26 constituting the admission side for the ram 34, O-ring seals can be provided which can be applied onto a film seal likewise applied to the admission side of the magazine 26. When that end of the ram 34 opposite the admission side of the magazine 26 is driven into a corresponding hollow space 40, the film seal or a layer of sealing lacquer is pierced through. A film seal or a layer of sealing lacquer can also be applied on the exit side for the test element 42. This is pushed out by the advance movement of the test element 42 from the hollow spaces 40 and also pierces through the layer of sealing lacquer or the film seal provided on this side. Moreover, the elastic sealing elements 70 in the form of sealing lips on the exit side in FIGS. 5.1 and 5.2 function as a seal during the pushing-out movement of the test element 42. The fact that the individual hollow spaces 40 in the magazine 26 are separated from one another by dividing walls rules out the possibility of contamination of the test elements 42 stored in the magazine 26 through an opened hollow space 40 during the phase in which the test elements 42 are pushed out from said hollow space 40.

Figure 6:
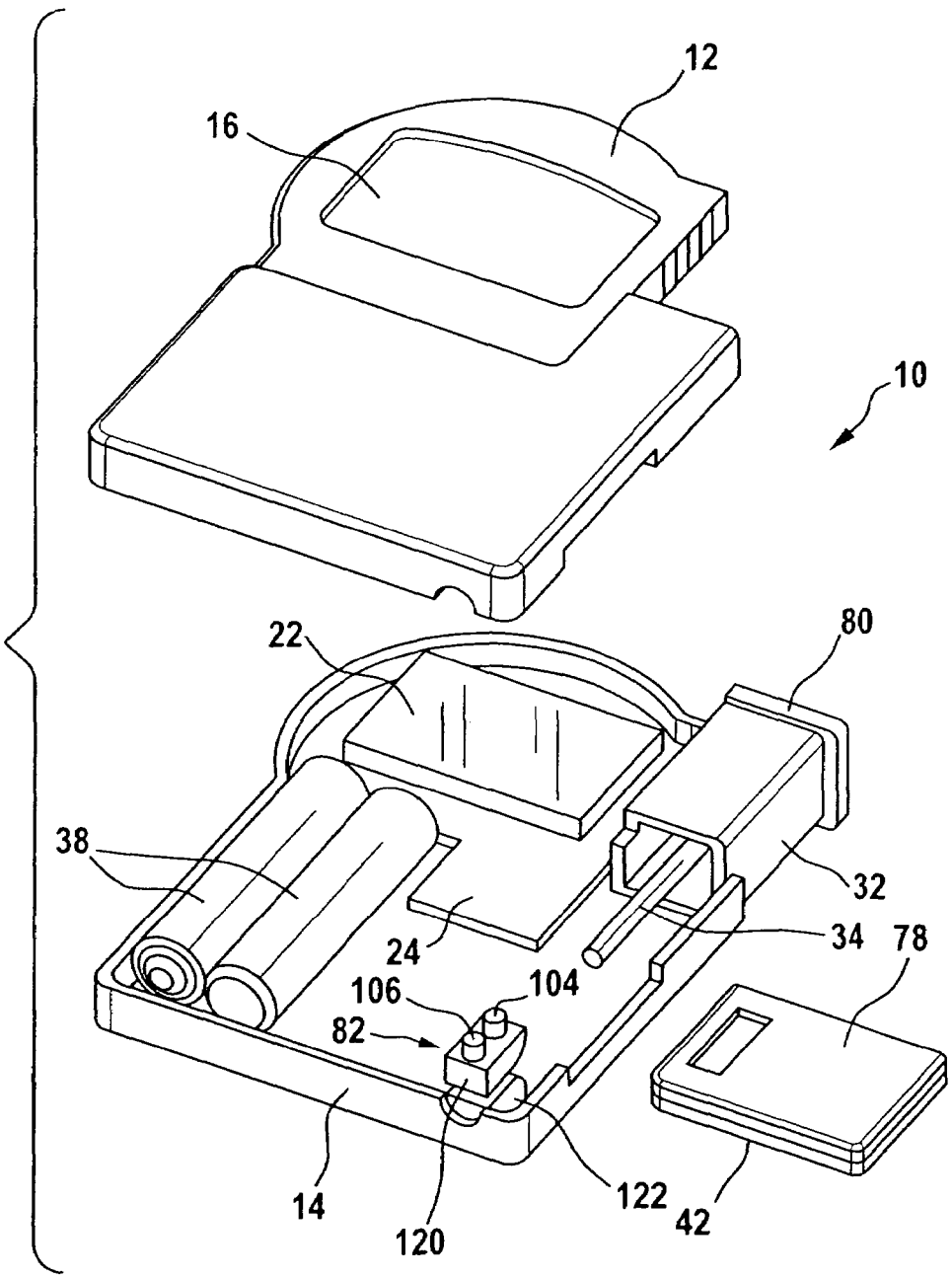
FIG. 6 is an exploded perspective view of another illustrative embodiment of a portable analysis appliance or analysis system.

FIG. 6 shows a further illustrative embodiment of the portable analysis appliance proposed according to the invention.

The exploded view in FIG. 6 shows that the upper shell 12 has an opening 16. The opening 16 corresponds substantially to the dimensions of a display screen 22 arranged on the circuit board 24 in the lower shell 14. The evaluation electronics of the portable analysis appliance 10 in FIG. 6 are not shown in detail. The batteries 38 used for supplying power to the portable analysis appliance 10 are depicted. These are fitted into a battery seat in the lower shell 14 of the portable analysis appliance 10. Moreover, in the lower shell 14 there is also a grip element 32 designed in the manner of a plunger with a press surface 80. The grip element 32 in the form of a plunger encloses a rod-shaped ram 34 which is used to push out the test elements 42 contained inside a stationary magazine 78. Lying opposite the rod-shaped ram 34, a guide identified by reference number 82 is arranged in the lower shell 14. The guide 82 mainly comprises a first abutment part 120 and a second abutment part 122. Each of the two abutment parts 120, 122 is acted upon by a pair of adjusting springs 104, 106, such that the gap present between the two abutment parts 120, 122 is variable. The springs 104 and 106 on the first abutment part 120 are supported on the inner side of the upper shell 14, while the adjusting springs 104 and 106 that each act on the second abutment part 122 (and are not shown in FIG. 6) are supported on the inner side of the lower shell 14 of the portable analysis appliance 10.

FIG. 7 shows the assembled state of the portable analysis appliance 10 according to the view in FIG. 6. The display screen 22 can be read off through the opening 16 in the upper shell 12 of the portable analysis appliance 10. The upper shell 12 and the lower shell 14 adjoin one another along a parting line 52. Correspondingly configured recesses in the upper shell 12 and in the lower shell 14 define an output opening 94 for the test elements 42 pushed out from the portable analysis appliance 10, and also define the insertion opening 92 of rectangular cross section for the stationary magazine 78, which is pushed into the portable analysis appliance 10 in insertion direction 48. It will also be seen from the view according to FIG. 7 that the plunger-shaped grip element 32 is located in its deactivated position, such that the ram 34 enclosed by it is inactive. Reference number 80 designates the manually actuated press surface of the plunger-shaped grip element 32.

The view according to FIG. 7.1 is an enlarged view of the stationary magazine 78 in the form of a stack magazine. In addition to the code key surface arranged on the top face of the stationary magazine 78 for the reading-out of batch-specific information by the evaluation electronics of the portable analysis appliance 10, the stationary magazine 78 also comprises a movable closure element 96. This can be opened in the direction of the arrow 98, so that an output opening for the test element 42 from the stationary magazine 78 is created. The closure element 96 can be designed as a plastic component which, when the stationary magazine 78 is in the used state, prevents entry of air moisture into the stationary magazine 78. By contrast, after the closure element 96 has been opened, it is easy to push the test element 42 out of the stationary magazine 78.

FIG. 8.1 shows the portable analysis appliance 10 in the assembled state, in which the plunger-shaped grip element 32 and press surface 80 are shown in their deactivated position, i.e. in this state of the analysis appliance 10 no test element 42 is presented at the output opening 94 of the portable analysis appliance 10. In the view according to FIG. 8.2, the plunger-shaped grip element 32 is shown in the state in which it has been driven into the portable analysis appliance 10. This state is reached by pressing on the press surface 80, as a result of which a force 102 acts on the plunger-shaped grip section 32 such that the latter is driven into the housing of the portable analysis appliance 10 comprising the upper shell 12 and lower shell 14. From the stationary magazine 78 that has been pushed into the insertion opening 92, the next test element 42 that can be pushed out by the movable ram 34 is presented at the output opening 94, this being indicated in FIG. 8.2 by reference number 100. For the sake of completeness, it should be noted that the upper shell 12 and lower shell 14 lie against one another along the parting line 52. The parting line can also be designed, for example, as a labyrinth seal in order to minimize as far as possible the entry of air moisture into the interior of the portable analysis appliance 10.

The view according to FIG. 9.1 shows an alternate guide 82 that is arranged lying opposite the stationary magazine 78. According to the view in FIG. 9.1, the guide 82 comprises the first abutment part 120 and the second abutment part 122. The two mutually facing sides of the first abutment part 120 and second abutment part 122 delimit a gap which, in the view according to FIG. 9.1, has a narrow gap width 108. Each of the abutment parts 120 and 122 is acted upon by a pair of adjusting springs 104, 106, as a result of which the two abutment parts 120, 122 are movable relative to one another. With the stationary magazine 78 pushed into the portable analysis appliance 10, its output side, i.e. the side at which the test element 42 is pushed out, lies opposite the guide 82. By contrast, the ram 34 lies with its front face opposite the long side oriented away from the output side of the stationary magazine 78. The first abutment part 120 and the second abutment part 122 each comprise run-in bevels 86 and 88, respectively, which define a run-in funnel 84.

It will be seen from FIG. 9.2 that the ram 34 for pushing out the test element 42 has been pushed partially into the stationary magazine 78. Because of this, the test element 42 is pushed out of the latter along an axis in an orientation corresponding to the storage position in the stationary magazine 78. The test elements 42 inside the stationary magazine 78 are preferably held in an inclined position, for example inclined by 45° relative to the base surface of the stationary magazine 78. Because of this, the test element 42 gripped by the ram 34 emerges from the stationary magazine 78 in this inclined position. The test element 42 runs up against the run-in bevels 86 and 88 of the abutment parts 120 and 122 acted upon by the adjusting springs 104, 106 and increases the gap between these from the narrow gap width 108 to the wide gap width 110 shown in FIG. 9.2.

FIG. 9.3 shows a view of the inside of the stationary magazine 78. The view in FIG. 9.3 shows, on the one hand, the 45° orientation 114 (storage position) of the test element 42 inside the stationary magazine 78 and, on the other hand, the delivery mimic of the test element 42 inside the stationary magazine 78. According to the view in FIG. 9.3, pretensioning elements 28, which can be designed for example as helical springs, are arranged inside the stationary magazine 78. A pair of helical springs 28 act on an abutment 112 whose side directed away from the pretensioning elements 28 faces towards the store of test elements 42. These are accordingly held pretensioned at all times inside the stationary magazine 78, so as to ensure that, when the ram 34 is moved into the stationary magazine 78, a new test element 42 can always be pushed out and moves into the guide 82.

The view according to FIG. 9.3 shows the first abutment part 120 in a partially sectioned view. The first abutment part 120 acted upon by the adjusting springs 104 and 106 comprises a rounded part 124 onto which the leading end of the test element 42 pushed out of the stationary magazine 78 runs. A force is applied to the test element 42 by the advance movement of the ram 34. As it is pushed farther into the narrow gap 108 delimited by the first abutment part 120 and second abutment part 122, the test element 42 running onto the run-in bevels 86 and 88 widens this narrow gap 108 to the wide gap width 110 shown in FIG. 9.2 and in so doing passes the rounded parts 124 which are formed on the first abutment part 120 and on the second abutment part 122 in order to ensure that the inclined test element 42 gripped by the ram 34 is transported gently through the guide 82.

It will be seen from the view according to FIG. 9.4 that, after the test element 42 has been completely pushed along an axis out of the stationary magazine 78 by the ram 34, it is converted to a horizontal orientation 116. As soon as the test element 42 has been pushed out of the stationary magazine 78 by the front face of the ram 34, it is converted from its storage position, which corresponds to the 45° orientation 114 shown in FIG. 9.3, to the horizontal orientation 116. This is a result of both the first abutment part 120 and also the second abutment part 122 being acted upon by the adjusting springs 104, 106. The widened gap width 110 shown in FIG. 9.2 is converted to the narrow gap width 108, which is defined by the thickness of the test element 42. In the state shown in FIG. 9.4, the rounded parts act on the top face and bottom face of the test element 42, so as to ensure that the latter is fixed by the guide 82 in a manner that is gentle on its material.

The figure sequence presented in FIGS. 9.5 to 9.8 shows the transport of the test element 42 out of the stationary magazine 78 and the advance of the test element 42 by the guide 82.

In the view according to FIG. 9.5, the first abutment part 120 and the second abutment part 122, each acted upon by a pair of adjusting springs 104 and 106, are set towards one another, i.e. a narrow gap 108 is present. In this state, the ram 34 has not yet been pushed into the stationary magazine 78, which is preferably a stack magazine. The run-in funnel 84 is defined by the first run-in bevel 86 and second run-in bevel 88 on the first abutment part 120 and second abutment part 122, respectively.

It will be seen from FIG. 9.6 that the ram 34 has been pushed partially into the stationary magazine 78. A test element 42 held at a 45° orientation 114 (storage position) in the stationary magazine 78 is pushed along an axis out of the latter by the front face of the ram 34. In the view according to FIG. 9.6, the edges of the leading end of the test element 42 make contact with the run-in bevels 86, 88 of the first abutment part 120 and second abutment part 120, respectively. There is still, as before, a narrow gap 108 between the mutually facing sides of the first abutment part 120 and of the second abutment part 122.

FIG. 9.7 shows a further advance of the ram 34 and, accordingly, onward delivery of the leading end of the test element 42. By its passing through the run-in funnel 84 delimited by the first run-in bevel 86 and second run-in bevel 88, the first abutment part 120 and the second abutment part 122 move counter to the action of the adjusting springs 104 and 106. The test element 42, gripped by the ram 34 and still in its storage position 114 in the stationary magazine 78, is now pushed between the pretensioned abutment parts 120 and 122 of the guide 82. FIG. 9.8 shows that the entire length of the test element 42 has now been pushed completely out of the stationary magazine 78, through which the ram 34 now fully extends. Because of the spring support of the first abutment part 120 and of the second abutment part 122 by the adjusting springs 104, 106, the test element 42 is turned about its longitudinal axis from its 45° orientation 114 (storage position) to a horizontal position 116 (presentation position) according to the view in FIG. 9.8. In the presentation position 116 or 100 (compare FIG. 8.2), the test element 42 can be used by the person using the portable analysis appliance 10, as in FIG. 8.2.

The two illustrative embodiments of the concept forming the basis of the invention have the effect that test elements 42 held in a stationary magazine 78 are protected against entry of air moisture, and a very high packing density of the test elements 42 inside the stationary magazine 78 can be achieved, so that a quantity of test elements 42 covering several days can be incorporated into a portable analysis appliance 10, without the test elements 42 being contaminated by air moisture and thus being rendered unusable. As a result of the turning movement of the test elements 42 after they have been pushed out of the stationary magazine 78, it can be in a manner that is comfortable for users of the portable analysis appliance 10. The turning movement may be described as being either about the longitudinal axis of the test element 42 or about the axis of movmement of the test element 42 out of the stationary magazine 78. As was the case with the embodiment of FIGS. 4.1 through 4.5, these two axes may be coaxial.

FIGS. 10.1 and 10.2 show a sealing element designed in the manner of a flap and used for a magazine held in a stationary position in the housing of a portable analysis appliance or of a portable analysis system.

FIG. 10.1 shows the stationary magazine 78 whose long side for admission of the ram 34 is identified by reference number 138, and whose long side for pushing out of the test elements is identified by reference number 140. A sealing flap 130 is mounted pivotably on the stationary magazine 78 via a hinge 132 and is located in its sealing position 142 in the view according to FIG. 10.1. The seal gap between the stationary magazine 78 and the sealing flap 130 is identified by reference number 136. On the long side 138 for admission into the stationary magazine 78, the ram 64 is pushed into an insertion opening 134 in which a preferably annular sealing element is located. In the inside of the stationary magazine 78 according to the view in FIG. 10.1, the test element 42 (see view according to FIG. 9.3) is held in an inclined position 114 (storage position).

When the ram 34 is driven in the direction of forward stroke 74 into the insertion openings 134, a coupling with the hinge 132 for the sealing flap 130, for example according to the slide coupling principle, opens the sealing flap 130 in line with the forward stroke 74 of the ram 34 via grip element 32.

In the view according to FIG. 10.2, the sealing flap in the stationary magazine is in its release position. According to the view in FIG. 10.2, the ram 34 has been driven completely into the stationary magazine 78 and has gripped the test element 42 inside the slit 64 and has moved it into a pushed-out position 146. The sealing flap 130 now situated in its release position 144 is opened only so far for the test element 42 to be able to emerge from it. Because of the coupling of the sealing flap 130 to the reciprocating movement of the ram 34, the sealing flap is returned to its sealing position in FIG. 10.1 when the ram 34 is drawn out from the stationary magazine 78 via corresponding actuation of the grip element 32.

Inside the insertion opening 134, long-term sealing of the stationary magazine 78 against entry of air moisture can be achieved if, in addition to a sealing lip in the manner of an O-ring inside the insertion opening 134, a sealing lacquer or a film seal is applied to an area of the admission side 138 covered by the insertion opening 134, and, when the stationary magazine 78 is used for the first time, this sealing lacquer or film seal can be pierced by the slit 64 of the ram 34.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A portable analysis appliance, including:
   a housing;
   a magazine having an interior configured to hold test elements; and
   a delivery device configured to deliver the test elements from a storage position in the interior of the magazine to a presentation position lying at least partially outside the magazine and at least partially inside the housing, the presentation position being a position where the test element is presented to a user ready for use;
   wherein the delivery of the test elements from the magazine includes a first movement out of the interior of the magazine and a second movement by means of a guide into the presentation position, each test element, during movement of the test element in a transportation direction, being rotated about a longitudinal axis which is substantially parallel to the transportation direction.

2. The portable analysis appliance of claim 1, wherein the test elements are substantially upright relative to horizontal when in the storage position.

3. The portable analysis appliance of claim 1, wherein the test elements are in an inclined orientation relative to horizontal when in the storage position.

4. The portable analysis appliance of claim 1, wherein the test elements are in a substantially horizontal position at an output opening of the housing when in the presentation position.

5. The portable analysis appliance of claim 1, wherein the second movement is a rotary movement.

6. The portable analysis appliance of claim 1, wherein the delivery device includes a ram which can be actuated manually via a grip element and, when the ram is driven in an advance movement relative to the magazine, a test element is pushed out of this magazine.

7. The portable analysis appliance of claim 1, wherein the magazine has an engagement structure against which a transport pawl engages for controlling movement of the magazine in an advance direction inside the housing.

8. The portable analysis appliance of claim 7, wherein the transport pawl has catches which are arranged with an offset relative to one another.

9. The portable analysis appliance of claim 7, wherein the engagement structure extends substantially parallel to the advance direction and includes a plurality of teeth having run-in bevels and contact faces.

10. The portable analysis appliance of claim 9, wherein the run-in bevels and the contact faces are formed on long sides of the engagement structure.

11. The portable analysis appliance of claim 6, wherein the guide imparts a turning movement to the ram as the ram is guided axially by the guide.

12. The portable analysis appliance of claim 11, wherein the guide at least partially encloses the ram and has a curved section which imparts the turning movement to the ram after the test element is pushed out of the magazine.

13. The portable analysis appliance of claim 6, wherein the ram includes an end remote from the magazine, the end having a bent portion.

14. The portable analysis appliance of claim 6, wherein the ram includes a receiving opening configured to engage the test element.

15. The portable analysis appliance of claim 14, wherein the receiving opening is formed as a slit in the ram.

16. The portable analysis appliance of claim 11, wherein the ram imparts the turning movement to the test element during movement of the test element from the storage position in a receiving space of the magazine to the presentation position, the turning movement extending through approximately 90 degrees.

17. The portable analysis appliance of claim 7, wherein the transport pawl is coupled to a grip element at least during an initial phase of a forward stroke of the grip element.

18. The portable analysis appliance of claim 1, wherein the magazine further includes elastic sealing elements configured to seal off the interior of the magazine against entry of air moisture both in an unused state of the magazine and after removal of a test element.

19. The portable analysis appliance of claim 18, wherein the elastic sealing elements include sealing lips which seal off receiving spaces for the test elements in the magazine and seal against the test elements as the test elements are moved from the magazine.

20. The portable analysis appliance of claim 1, wherein the test elements are held in the magazine by a spring.

21. The portable analysis appliance of claim 1, wherein the guide is positioned inside the housing and includes bodies which lie opposite one another and define at least one gap width.

22. The portable analysis appliance of claim 21, wherein at least one of the bodies is mounted resiliently in the housing.

23. The portable analysis appliance of claim 21, wherein at least one of the bodies has a run-in bevel configured as a guide surface.

24. The portable analysis appliance of claim 21, wherein the bodies define a run-in funnel for the test elements.

25. The portable analysis appliance of claim 21, wherein each body has a side facing the other body, at least one of the sides having a rounded part configured as a guide surface for the test elements.

26. The portable analysis appliance of claim 1, wherein the magazine includes a side that is sealed off against entry of air moisture by one of a film seal and a layer of sealing lacquer.

27. A portable analysis appliance, including:
   a magazine having an interior configured to hold each of a plurality of test elements in a storage position;
   a delivery device having a ram configured to move a test element in a transportation direction from the storage position to a presentation position, the presentation position being a position where the test element is presented to a user ready for use; and
   a guide having a surface that interacts with one of the test element and the ram to cause rotation of the test element about a longitudinal axis of the test element that is substantially parallel to the transportation direction during movement from the storage position to the presentation position.

28. The portable analysis appliance of claim 27, wherein the test element is held at an angle relative to horizontal when in the storage position and is held in a substantially horizontal orientation when in the presentation position.

29. The portable analysis appliance of claim 27, wherein the ram is manually movable into the magazine to push the test element out of the magazine along an axis of movement.

30. The portable analysis appliance of claim 29, wherein the guide causes rotation about the axis of movement of the test element during movement from the storage position to the presentation position.

31. The portable analysis appliance of claim 27, further including a transport pawl configured to engage an engagement structure of the magazine to control advancement of the magazine in an advance direction.

32. The portable analysis appliance of claim 27, wherein the guide includes a pair of opposed bodies that define a gap for receiving the test strip.

33. The portable analysis appliance of claim 32, wherein each body includes a bevel, the bevels together defining a run-in funnel configured to rotate the test strip from the storage position to the presentation position.

34. A portable analysis appliance, including:
   a housing;
   means disposed in the housing for holding each of a plurality of test elements in a storage position;
   means for moving the test elements in a transportation direction from the storage position to a presentation position, the presentation position being a position where one of the test elements is presented to a user ready for use; and means for guiding the test elements through a rotational movement about a longitudinal axis of the test elements substantially parallel to the transportation direction during movement from the storage position to the presentation position.

* * * * *